United States Patent
Jiang et al.

(10) Patent No.: US 11,944,636 B2
(45) Date of Patent: Apr. 2, 2024

(54) MEDICINAL COMPOSITION COMPRISING A NON-CODING RNA MOLECULE AND AN ANTIBODY TARGETING A TUMOR ANTIGEN

(71) Applicant: Macau University of Science and Technology, Taipa (MO)

(72) Inventors: Zhi-Hong Jiang, Taipa (MO); Lee-Fong Yau, Taipa (MO); Tian-Tian Tong, Taipa (MO); Hao Huang, Taipa (MO); Kua Hu, Taipa (MO); Elaine Lai-Han Leung, Taipa (MO)

(73) Assignee: Macau University of Science and Technology, Taipa (MO)

( * ) Notice: Subject to any disclaimer, the term of this patent is extended or adjusted under 35 U.S.C. 154(b) by 210 days.

(21) Appl. No.: 17/094,903

(22) Filed: Nov. 11, 2020

(65) Prior Publication Data
US 2022/0088055 A1 Mar. 24, 2022

(30) Foreign Application Priority Data
Sep. 17, 2020 (CN) .......................... 202010978553.X

(51) Int. Cl.
| | | |
|---|---|---|
| *C07H 21/04* | (2006.01) | |
| *A61K 31/7105* | (2006.01) | |
| *A61K 31/713* | (2006.01) | |
| *A61P 35/00* | (2006.01) | |
| *C07K 16/28* | (2006.01) | |

(52) U.S. Cl.
CPC ........ *A61K 31/7105* (2013.01); *A61K 31/713* (2013.01); *A61P 35/00* (2018.01); *C07K 16/2818* (2013.01)

(58) Field of Classification Search
None
See application file for complete search history.

(56) References Cited

U.S. PATENT DOCUMENTS 11,149,271 B2 * 10/2021 Jiang ..................... C12N 15/11
2020/0071695 A1 3/2020 Jiang et al.

OTHER PUBLICATIONS

Palanca-Wessels, Maria C., et al. "Antibody targeting facilitates effective intratumoral siRNA nanoparticle delivery to HER2-overexpressing cancer cells." (2016): 9561.*
Dou, Shuang, et al. "Anti-Her2 single-chain antibody mediated DNMTs-siRNA delivery for targeted breast cancer therapy." Journal of controlled release 161.3 (2012): 875-883.*
Zhang SJ, Ren SX. Novel Immuno-oncology Therapy: Current Status of Clinical Research and Prospect of Application. Zhongguo Fei Ai Za Zhi, 2017, 20(9): 645-651.

* cited by examiner

*Primary Examiner* — Kimberly Chong
(74) *Attorney, Agent, or Firm* — Renner, Kenner, Greive, Bobak, Taylor & Weber

(57) ABSTRACT

This invention discloses a medicinal composition includes a non-coding RNA molecule and an antibody targeting a tumor antigen for preventing and/or treating cancer. This invention uses the synergistic combination of a non-coding RNA molecule or its functional variant or homologue, and an antibody targeting a tumor antigen to prevent and/or treat cancer, thereby providing a novel and effective method in preventing and/or treating various cancers.

15 Claims, 3 Drawing Sheets
Specification includes a Sequence Listing.

MEDICINAL COMPOSITION COMPRISING A NON-CODING RNA MOLECULE AND AN ANTIBODY TARGETING A TUMOR ANTIGEN

TECHNICAL FIELD

This invention relates to biopharmaceutical field, specifically a medicinal composition comprising a non-coding RNA molecule and an antibody targeting a tumor antigen, as well as use thereof. This invention further relates to a method of preventing and/or treating cancer in a subject in need thereof. This invention further relates to a kit comprising the medicinal composition.

SEQUENCE LISTING

The Sequence Listing file entitled "sequencelisting" having a size of 619 bytes and a creation date of Nov. 11, 2020, that was filed with the patent application is incorporated herein by reference in its entirety.

BACKGROUND

Cancer has become the top leading cause of death globally. Small molecules such as alkaloids, terpenoids and flavonoids have been widely used for treating cancers. For instance, some alkaloids are found to inhibit cancer by enhancing the effect of other anti-cancer drugs. However, most of them are toxic to human. Moreover, macromolecules such as DNAs, RNAs and proteins are intrinsically unstable and exhibit poor bioactivity. Therefore, they have not been widely applied in cancer treatment.

Currently, some studies showed that small non-coding RNAs (small ncRNAs) such as microRNAs exert diverse regulatory roles by targeting different aspects of RNA transcription or post-transcription process in nearly all eukaryotic organisms. Mlotshwa, S. et al. (*Cell research* 2015, 25 (4), 521-4) suggested that exogenous plant microRNAs derived from foods could be absorbed through the mammalian gastrointestinal tracts and then were delivered via the bloodstream to various organs, where they are capable of regulating the expression of mammalian genes. Goodarzi, H. et al. (*Cell* 2015, 161 (4), 790-802) revealed that endogenous tRNA-derived fragments could suppress the stability of multiple oncogenic transcripts in breast cancer cells through binding and antagonizing activities of pathogenesis-related RNA-binding protein.

Therapeutic anticancer monoclonal antibodies (mAbs) can target tumor-associated antigens (e.g. CD19, CD20, CD22 and Her2), epidermal growth factor receptor and vascular endothelial growth factor (e.g. EGFR, VEGF and VEGFR2), and key immune checkpoints molecules (e.g. CTLA4, PD-1 and PD-L1), etc. Their mechanisms of action against cancers are as below:
(1) Directly blockade of ligand-receptor signal transduction activity to induce apoptosis,
(2) Elicit immune cell-mediated cytotoxicity including antibody-dependent cell phagocytosis (ADCP), antibody-dependent cell-mediated cytotoxicity (ADCC) and complement-dependent cytotoxicity (CDC),
(3) Participate in the production of genetically modified tumor-specific T cells, e.g. single-chain variable Fragment (scFv) genetically engineered T cells,
(4) Blockade of key immune checkpoints molecules to reduce immune tolerance and induce T cells activation,
(5) Target to tumor vasculature and stroma to suppress vascular receptors or ligands, resulting in inhibition of tumor cells proliferation by inducing ablation of vasculature and stroma cells.

Monoclonal antibody therapy has unique advantages, including its high specificity towards cancer cells and minimal side effects. To date, about 30 monoclonal antibody drugs have been approved by the Food and Drug Administration (FDA) for clinical use in cancer therapy, including Rituximab (1997), Trastuzumab (1998), Durvalumab (2017), Inotuzumab ozogamicin (2017), Moxetumomab pasudotox (2018), and Cemiplimab-rwlc (2018). These monoclonal antibody drugs have indicated promising anti-cancer activity; however, resistance during long-term alone treatment is a major issue.

Comparsion of advantages and disadvantages among RNA drugs, antibodies and cell therapy

|  | RNA drugs | Antibodies | Cell therapy |
| --- | --- | --- | --- |
| Stability | Lower | Lower | High |
| Half-life | Short | Long | — |
| Specificity | Lower | High | High |
| Drug delivery | More difficult | Easier | Easier |
| Immunogenicity | Low | Higher | — |
| Side effects | Less | Less | More |
| Complexity in production | Low | High | Very high |
| Cost | Low | High | Very high |

Different from traditional therapies, immunotherapy is a type of cancer treatment that boosts human body's self-immune system to fight against cancer. For instance, immune checkpoint blockade targeting PD-1/PD-L1 signaling pathway can activate T-cell mediated tumor cytotoxicity, and eventually killing the tumor cells. Immunotherapy has promising therapeutic efficacy in a variety of tumors and substantively improves overall survival in patients. Nevertheless, the overall clinical objective response rate of PD1/PD-L1 blockade therapy was only about 20%, and varying response rates among different cancers was obvious. The efficacy of PD1/PD-L1 blockade therapy is closely related to PD-L1 expression level, tumor mutation burden (TMB), defective mismatch repair (dMMR) or microsatellite instability (MSI), number of tumor-infiltrating lymphocytes, and intestinal microbiome, etc. The efficacy of treatment with single PD-1 inhibitor in most unselected solid tumors was only 10%-30%, and it might cause the incidence of serious side effects, especially immune-mediated pneumonitis and immune myocarditis. Meanwhile, solely RNA interference therapy has the problem of off-target effect, induction of immune response. Therefore, it is still vital to explore more effective medicine to treat cancer.

SUMMARY OF THE INVENTION

In view of the above inadequacy of the existing techniques, the inventor has invented successfully a method of preventing and/or treating cancer by using a synergistic combination of a non-coding RNA molecule or its functional variant or homologue, and an antibody targeting a tumor antigen, thereby providing a novel and effective method in preventing and/or treating various cancers.

Besides, this invention provides a medicinal composition which prevents and/or treats cancer. The composition comprises a non-coding RNA molecule or its functional variant or homologue, and an antibody targeting a tumor antigen. In the medicinal composition, the mass ratio of the non-coding RNA molecule or its functional variant or homologues, and the antibody targeting tumor antigen is between 1:250 and 1:100, and preferably 1:125.

In the above medicinal composition, the non-coding RNA molecule is selected from the group consisting of a tRNA molecule, a miRNA molecule, a siRNA molecule, and any combination thereof. Preferably, the non-coding RNA molecule is a tRNA molecule. More preferably, the non-coding RNA molecule is a double-strand tRNA molecule. Advantageously, the double-strand tRNA molecule comprises an antisense strand of SEQ ID NO: 1 (5'-CAAACUGCUCUA-CUCCGCG-3') and a sense strand of SEQ ID NO: 2 (5'-CGCGGAGUAGAGCAGUUUG-3').

According to a specific embodiment of this invention, the double-strand tRNA molecule consists of an antisense strand of SEQ ID NO: 1 and a sense strand of SEQ ID NO: 2.

In the above medicinal composition, the antibody targets a tumor antigen selected from the group consisting of PD-L1, CD47, CD52, CTLA4, RANKL, CD19, CD20, CD22, CD30, CD33, CD38, CD147, GD2, EGFR, VEGF, PIGF, VEGFR, VEGFR2, PSMA, HER2, AXL, ROR2, PD-1, PDGF-Rα, SLAMF7, CCR4, and any combination thereof. Preferably, the antibody targets PD-1 pathway. More preferably, the antibody is an anti-PD-1 antibody.

According to an exemplary embodiment of this invention, the antibody is an anti-mouse PD-1 antibody.

According to this invention, the medicinal composition further comprises a pharmaceutically acceptable carrier, a diluent, or an excipient. Preferably, the pharmaceutically acceptable carrier comprises a gene delivery vector. Preferably, the pharmaceutically acceptable carrier comprises a material encapsulating the non-coding RNA molecule to form nanoparticles. More preferably, the pharmaceutically acceptable carrier is selected from the group consisting of a viral vector, a collagen, a polymer, a polypeptide, a protamine, a lipid-forming liposome, and any combination thereof. Advantageously, the pharmaceutically acceptable carrier comprises a polypeptide. Most preferably, the pharmaceutically acceptable carrier comprises a histidine-lysine polymer. When the antibody in the medicinal composition of this invention is used, it can be diluted to a certain concentration by using a diluent. For example, normal saline can be used to dilute the antibody to a certain concentration before drug administration.

The above medicinal composition may further comprise other medicine for preventing and/or treating cancer (e.g. an anticancer drug), and/or a nucleic acid stabilizer.

According to an exemplary embodiment of this invention, the medicinal composition has a dosage form for subcutaneous, intravenous, intraperitoneal, or intramuscular injection.

In another aspect, this invention also provides a kit which comprises the above medicinal composition. In the above kit, the non-coding RNA molecule or its functional variant or homologue, and an antibody targeting a tumor antigen are separately placed, e.g. they are provided in separate containers. More preferably, in the above kit, the non-coding RNA molecule or its functional variant or homologue, and the antibody targeting a tumor antigen are separately placed, and each of them is provided in a dosage form for subcutaneous, intravenous, intraperitoneal, or intramuscular injection.

In a further aspect, this invention provides use of the medicinal composition in the preparation of a medicament for preventing and/or treating cancer. Preferably, the cancer is selected from the group consisting of non-small cell lung cancer, lung squamous-cell carcinoma, malignant melanoma, Hodgkin's lymphoma, Merkel cell carcinoma, castrate-resistant prostate cancer, liver cancer, gastric cancer, renal cancer, colorectal cancer, bladder cancer, head and neck cancers, all microsatellite instability-high (MSI-H) cancer, and any combination thereof. More preferably, the cancer is lung cancer.

Accordingly, this invention also provides a method of preventing and/or treating cancer in a subject in need thereof, wherein the method comprises administering an effective amount of the above medicinal composition to the subject.

In the above use or method, the growth, proliferation, and/or metastasis of cancer cells or cancer tissues are inhibited. In particular, the medicinal composition is able to prevent and/or treat cancer by inhibiting growth of cancer cells and/or cancer tissues, and/or inhibiting proliferation and/or metastasis, e.g. inhibition of the growth, proliferation or metastasis of lung cancer cells or tissues.

According to an exemplary embodiment of this invention, in the above purpose or method, the cancer is lung cancer.

In the specific embodiment of this invention, the non-coding RNA molecule or its functional variant or homologue, and the antibody targeting the tumor antigen may be administered to the subject simultaneously or sequentially. According to an exemplary embodiment of this invention, the frequency, administration route and time of administering the non-coding RNA molecule or its functional variant or homologue, and the antibody targeting the tumor antigen can be arranged separately. For example, the frequency of administration of the non-coding RNA molecule or its functional variant or homologue, and the antibody targeting the tumor antigen can be once a day, once every two days or once every three days. Preferably, the frequency of administration of the antibody targeting the tumor antigen is once every three days, and the frequency of administration of the non-coding RNA molecule is once every two days. In a specific embodiment of this invention, the non-coding RNA molecule or its functional variant or homologue, and the antibody targeting the tumor antigen are administered to the subject simultaneously at the first day. Preferably, the non-coding RNA molecule or its functional variant or homologue, and the antibody targeting the tumor antigen may be administered to the subject via subcutaneous, intravenous, intraperitoneal, or intramuscular injection, wherein there is no special limitation on the dosage of administration of the antibody targeting the tumor antigen and it can be applied based on actual situation, e.g. condition of patients or types of antibody. For example, the dosage of antibody targeting the tumor antigen may be 6 mg-600 mg each time. In a preferred embodiment, the dosage of the antibody targeting the tumor antigen is 180 mg each time. The dosage of the non-coding RNA molecule or its functional variant or homologue may be between 30 μg/kg and 200 μg/kg each time, and is preferably between 50 μg/kg and 100 μg/kg each time. In a preferred embodiment, the dosage of the non-coding RNA molecule or its functional variant or homologue is 50 μg/kg or 100 μg/kg each time. There is no special limitation on the frequency of administration of the antibody targeting the tumor antigen and the antibody can be applied based on actual situation, e.g. condition of patients.

Specifically, the inventor found out that antibody targeting a tumor antigen especially anti-PD-1 antibody had a good suppression on lung cancer cells whereas no effects were observed when the non-coding RNA molecule was solely administered at different dosages. However, the growth of tumors in mice was suppressed (P<0.05) and their survival rates were elevated after administering with the anti-PD-1 antibody and non-coding RNA molecule synergistically. The experimental results of proliferation of macrophages RAW264.7 indicated that there was obvious proliferation of macrophages under a 200 nM of RNA molecule HC58. This elucidated that RNA molecule HC58 can activate macrophages and suppress the proliferation of tumor cells together with T cells.

In addition to those specifically described, those skilled in the art will understand that this invention described herein can be subjected to modification and changes. This invention includes all of these modifications and changes. This invention also includes all the steps or features, and any combination thereof, which are individually or collaboratively mentioned or indicated in the disclosure herein.

Other features and aspects of this invention will become apparent by consideration of the following detailed description and accompanying drawing.

DETAILED DESCRIPTION OF THE INVENTION

Figure 1:
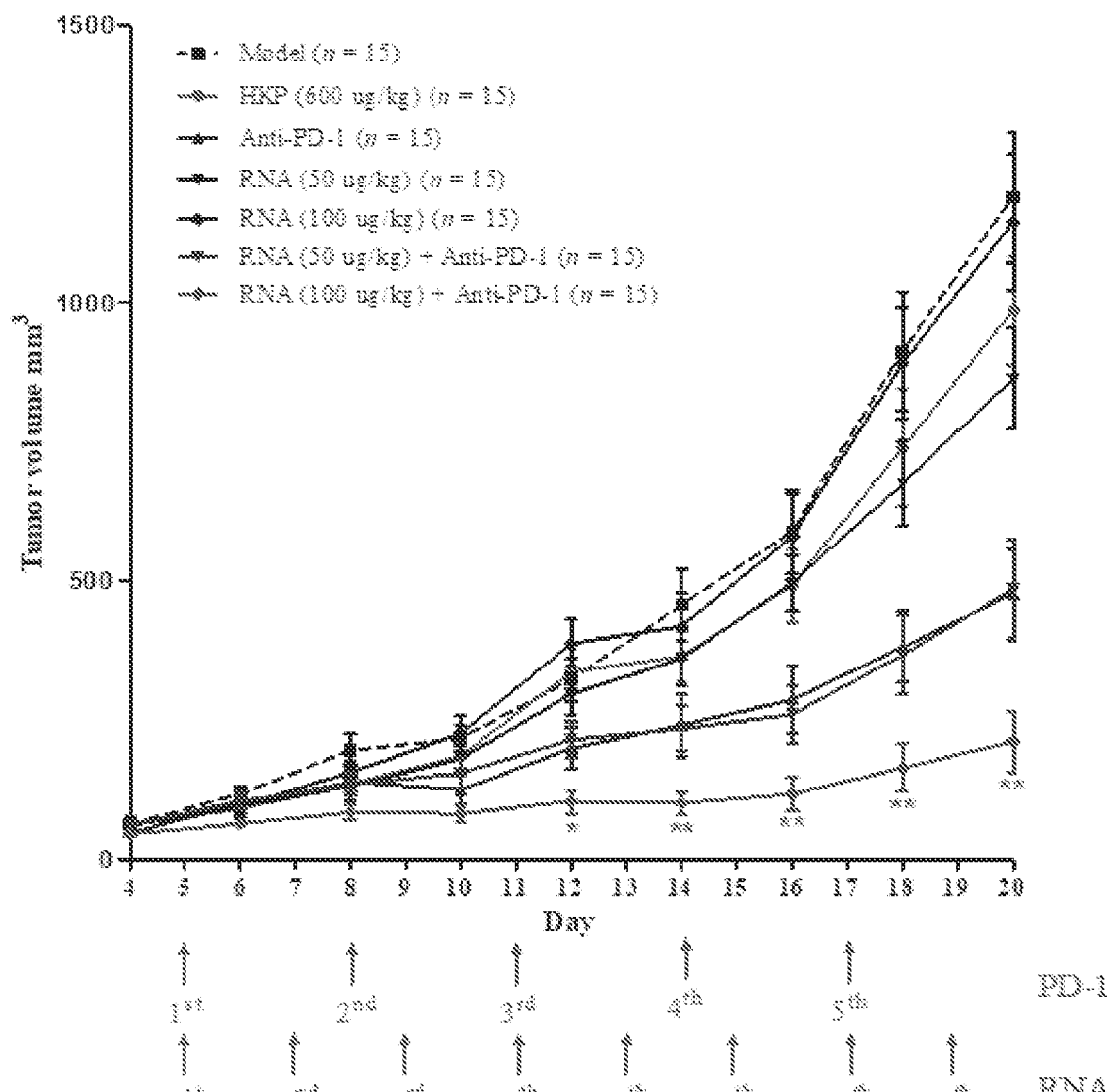
FIG. 1 shows the tumor growth curves of each group of models.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element.

This invention provides a method of preventing and/or treating a subject suffering from cancer comprising administration of an effective amount of the synergistic combination of a non-coding RNA molecule and an antibody targeting a tumor antigen. The non-coding RNA molecule administrated according to this invention may be naturally present, modified or artificially synthesized, and preferably the non-coding RNA molecule is isolated or derived from tRNA of plants. The non-coding RNA molecule of this invention is not provided in the form of boiled extract obtained from the plant such as decoction, as it would be appreciated that non-coding RNA molecule is susceptible to spontaneous degradation at elevated temperature, alkaline pH, and the presence of nuclease or divalent metal ions. In an embodiment, the non-coding RNA molecule and the gene delivery vector of this invention are also provided, wherein the details will be described later.

The non-coding RNA molecule of this invention comprises a nucleotide sequence selected from SEQ ID NO: 1 and SEQ ID NO: 2. The term "functional variant" of the RNA molecule refers to a molecule substantially similar to said RNA molecule with one or more sequence alterations that do not affect biological activity or function of the RNA molecule. The alterations in sequence that do not affect the functional properties of the resultant RNA molecules are well known in the art. For example, nucleotide changes which result in alteration of the -5'-terminal and -3'-terminal portions of the molecules would not be expected to alter the activity of the polynucleotides. In an embodiment, the RNA molecule of this invention comprises at least one modified nucleoside selected from inosine, 1-methyladenosine, 2-methyladenosine, $N^6$-methyladenosine, $N^6$-isopentenyladenosine, 2'-O-methyladenosine, $N^6$-acetyladenosine, 1-methylinosine, pseudouridine, dihydrouridine, or 2-methylthio-$N^6$-methyladenosine.

In particular, the functional variant of the RNA molecule has at least 80%, 81%, 82%, 83%, 84%, 85%, 86%, 87%, 88%, 89%, 90%, 91%, 92%, 93%, 94%, 95%, 96%, 97%, 98%, or 99% overall sequence identity to the non-variant RNA molecule according to this invention.

The term "homologue" used herein refers to nucleotides having a sequence identity of at least 50%, at least 60%, at least 70%, at least 80%, at least 90% or at least 95% to the RNA molecules according to this invention. In an embodiment, the homologue of the RNA molecule has at least 90%, 91%, 92%, 93%, 94%, 95%, 96%, 97%, 98%, or 99% overall sequence identity to the RNA molecule.

The non-coding RNA molecule of this invention is selected from a transfer RNA (tRNA) molecule, a ribosomal RNA molecule, a micro RNA molecule, a siRNA molecule, or a piwi-interacting RNA molecule, and preferably is a tRNA molecule. tRNA molecules are highly conserved RNAs with function in various cellular processes such as reverse transcription, porphyrin biosynthesis or the like. In a particular embodiment, the RNA molecule of this invention is a tRNA molecule or a functional variant or homologue comprising an antisense sequence of SEQ ID NO: 1 and a sense sequence of SEQ ID NO: 2; or the tRNA molecule or its functional variant or homologue comprising a sense sequence of SEQ ID NO: 1 and an antisense sequence of SEQ ID NO: 2.

In an embodiment of this invention where the double-stranded tRNA molecule is a small double-stranded tRNA molecule having a sequence length of from about 10 to about 30 base pairs, from about 15 to about 25 base pairs, from about 19 to about 22 base pairs, 19 base pairs or 22 base pairs.

In particular, in an embodiment of this invention, the tRNA molecule has an antisense sequence of SEQ ID NO: 1, and a complementary sense sequence of SEQ ID NO: 2. The inventors unexpectedly found that the synergistic combination of a non-coding RNA molecule and an antibody targeting a tumor antigen of this invention are particularly useful in preventing and/or treating lung cancer as described in detail below.

The non-coding RNA molecule of this invention is preferably isolated or derived from plant. For example, the non-coding RNA molecule of this invention is isolated or derived from the *Panax ginseng* C. A. Mey.

In more detail, the preferred sequences of the non-coding RNA molecules of this invention are listed in Table 1 below.

The antisense sequence of SEQ ID NO: 1 and the sense sequence of SEQ ID NO: 2 as shown in Table 1 are artificially synthesized in accordance with this invention. The antisense sequence is complementary to the sense sequence to form a tRNA fragment (tRF).

In addition, the RNA molecule of this invention may comprise 3' overhang, preferably comprise two 3' overhangs. The provision of the 3' overhang improves the stability of the RNA molecules.

TABLE 1

RNA molecules denoted as HC58 derived through artificial synthesis according to this invention.

| Code | SEQ ID NO. | Antisense sequence (5'-3') | SEQ ID NO. | Sense sequence (5'-3') |
|---|---|---|---|---|
| HC58 | 1 | CAAACUGCUCUACUCCGCG | 2 | CGCGGAGUAGAGCAGUUUG |

Antibody: an antibody can be selected from any antibodies known in the art, for example, any recombinant or naturally present antibodies, particularly antibodies suitable for therapeutic, diagnostic, or scientific purposes. In this invention, the term "antibody" is used in its broadest sense, and particularly includes monoclonal, polyclonal antibodies (including antagonists, and blocking or neutralizing antibodies), and antibodies with multiple epitope specificities. According to this invention, the term "antibody" typically comprises any antibodies known in the art (for example, IgM, IgD, IgG, IgA and IgE), such as naturally present antibodies, antibodies produced in the host organism by immunization; antibodies isolated and identified from naturally present antibodies or antibodies produced in host organisms by immunization, and recombinant antibodies produced by biomolecular methods known in the art, as well as chimeric antibodies, human antibodies, human-derived antibodies, bispecific antibodies, intracellular antibodies, i.e. antibodies expressed in cells and are optionally localized in specific cell compartment, as well as fragments and variants of the antibodies. Generally, an antibody is composed of a light chain and a heavy chain, each of which has a variable domain and a constant domain. The light chain is composed of a N-terminal variable domain VL and a C-terminal constant domain CL. In contrast, the heavy chain of an IgG antibody, for example, consists of a N-terminal variable domain VH and three constant domains CH1, CH2, and CH3. Single chain antibody can also be used according to this invention. The antibody preferably comprises a full-length antibody, that is, an antibody composed of a complete heavy chain and a complete light chain, as described above. However, derivatives of an antibody, such as antibody fragment, variant or adduct can also be used as the antibody targeting a tumor antigen according to this invention. Antibody fragment can be selected from Fab, Fab', F(ab')2, Fc, Facb, pFc', Fd and Fv fragments of the aforementioned (full-length) antibodies. Generally, antibody fragment is known in the art. For example, Fab ("fragment or antigen-binding fragment") consists of a constant domain and a variable domain of each heavy and light chain. The two variable domains bind to epitopes on specific antigens. The two chains are connected by disulfide bonds. A scFv ("single chain variable fragment") fragment, for example, typically consists of the variable domains of the light chain and heavy chain. The domains are connected by artificial linkages, usually polypeptides, such as peptides comprising 15-25 glycine, proline and/or serine residues.

In the case of this invention, the term "combination of a non-coding RNA molecule and an antibody targeting a tumor antigen" preferably refers to a composition comprises at least one non-coding RNA molecule or its functional variant or homologue thereof, and at least one antibody targeting a tumor antigen and any combination thereof. Therefore, the RNA molecule/antibody composition can exist as a composition comprising all these components in a mixture (e.g. in a medicinal composition), or it can exist as a kit encompass multiple components, wherein different components form the kit with different components. By using a non-coding RNA molecule as a key component, the non-coding RNA molecule/antibody composition of this invention can elicit an adaptive immune response (and optionally an innate immune response) in a subject (preferably a mammal) to be treated. The antibody targeting a tumor antigen in the non-coding RNA molecule/antibody composition of this invention can antagonize specific pathway signal transduction by inhibiting or suppressing receptor-mediated signal transduction. Therefore, the administrated non-coding RNA molecule and antibody can act on the same or different targeting sites simultaneously or staggered in time. The non-coding RNA molecule/antibody composition can induce an active immune response, for example, thereby preventing tumor growth or inducing tumor regression. Therefore, the non-coding RNA molecule/antibody composition of this invention is suitable for effectively stimulating an antigen-specific immune response against cancer cells. More precisely, the non-coding RNA molecule/antibody composition of this invention is particularly suitable for treating cancers related to the overexpression of the antigen targeted by the antibody, and further improving the immune response against the tumor cells.

This invention is based on the following novel findings: the combination of a non-coding RNA molecule and an antibody targeting a tumor antigen in this invention exhibited obvious inhibition in tumor growth and elevation in survival rate. Therefore, the use of a non-coding RNA molecule, such as tRNA (transfer RNA), together with antibody targeting the members of the PD-1 pathway (especially the PD-1 receptor or its ligands PD-L1 and PD-L2) could effectively reduce the harmful effect of the disease to be treated (e.g. the growth rate of tumors). In this case, the inventor found that a treatment with the combination of a non-coding RNA molecule and an antibody targeting a tumor antigen is capable of inhibiting tumor growth and improving the survival rate of tumor-bearing mice in a synergistic manner. This was confirmed by the experimental data disclosed in the embodiment herein.

Turning back to the method of treatment, the method comprises the step of administering an effective amount of the combination of a non-coding RNA molecule and an antibody targeting a tumor antigen as described above to the subject suffering from cancers. In an embodiment, the step of administering the combination of a non-coding RNA molecule and an antibody targeting a tumor antigen to the subject comprises contacting cancer cells of the subject with the combination of a non-coding RNA molecule and an antibody targeting a tumor antigen.

The term "cancer" describes a physiological condition in subjects in which the cell population is characterized by uncontrolled growth of malignant (cancerous) cells. In an embodiment, the cancer to be treated is non-small cell lung cancer, lung squamous cell carcinoma, malignant melanoma, Hodgkin's lymphoma, Merkel cell carcinoma, castration-resistant prostate cancer, liver cancer, gastric cancer, renal cancer, colorectal cancer, bladder cancer, head and neck cancers, all microsatellite instability-high (MSI-H) cancer, and any combination thereof. In a specific embodiment, the cancer is lung cancer. In an alternative embodiment, the combination of a non-coding RNA molecule and an antibody targeting a tumor antigen in this invention can effectively treat cancer caused by LLC-LUC lung cancer xenografts in mice.

The term "subject" used herein refers to a living organism and can include but is not limited to a human being and an animal. The subject is preferably a mammal, more preferably a human being or a mouse. The combination of a non-coding RNA molecule and an antibody targeting a tumor antigen may be administered through injection to the subject, preferably a human or a mouse. The term "injection" encompasses intravenous, intramuscular, intraperitoneal, subcutaneous, and intradermal administration. In an embodiment, the RNA molecule of this invention is administered together with suitable excipient(s) to the subject through intravenous injection. For instance, the RNA molecule may be delivered to the subject or cell via transfection, electroporation, or viral-mediated delivery. In an embodiment, the antibody targeting a tumor antigen in this invention is administered together with the suitable excipient(s) to the subject through intraperitoneal injection.

The expression "effective amount" generally denotes an amount sufficient to produce prevention and/or therapeutically desirable results, wherein the exact nature of the result varies depending on the specific condition which is treated. In this invention, cancer is the condition to be prevented and/or treated, therefore the result is usually an inhibition of the growth, proliferation or metastasis of cancer cells, a reduction of cancer cells or the amelioration of symptoms related to the cancer cells, especially an inhibition of the proliferation of the cancer cells or induction of cell death, i.e. apoptosis of cancer cells. In an embodiment where the cancer is metastatic, the result is usually an inhibition of migration of cancer cells, suppression of the invasion of cancer cells to other tissues, inhibition of forming metastasis cancer cells at a secondary site distant from the primary site, or amelioration of symptoms related to metastatic cancer. In this invention, the effective amount of the combination of a non-coding RNA molecule and an antibody targeting a tumor antigen may depend on species, body weight, age and individual condition of the subject and can be determined by standard procedures with cell cultures or experimental animals.

The term "frequency of administration" refers to the frequency of administration of the medicinal composition disclosed herein at a given time. The frequency of administration can be indicated as the number of doses at a given time, for example, once a day, once every two days.

The combination of a non-coding RNA molecule and an antibody targeting a tumor antigen in this invention may be administered in form of a pharmaceutical composition comprising a non-coding RNA molecule, an antibody targeting a tumor antigen, and at least one pharmaceutically tolerable excipient. The pharmaceutically tolerable excipient may be one or more of a diluent, a filler, a binder, a disintegrant, a lubricant, a coloring agent, a surfactant, and a preservative. The pharmaceutical composition can be present in solid, semisolid, or liquid form, preferably in liquid form. The pharmaceutical composition can be liposome freeze-dried powder, polypeptide nanometer freeze-dried powder, spray, or tablet. The pharmaceutical composition may comprise further pharmaceutical effective ingredients such as therapeutic compounds which are used for treating cancer, such as cisplatin, carboplatin, paclitaxel, gemcitabine and/or vinblastine. The skilled technician is able to select suitable pharmaceutically tolerable excipients depending on the form of the pharmaceutical compositions and is aware of methods for manufacturing pharmaceutical compositions as well as able to select a suitable method for preparing the pharmaceutical composition depending on the kind of pharmaceutically tolerable excipients and the form of the pharmaceutical composition.

In an embodiment, non-coding RNA molecules provided as a composition containing a gene delivery vector. The gene delivery vector is any molecule that act as a carrier to deliver a gene to a cell. In embodiments where non-coding RNA molecule are transfected into cells, gene delivery vectors are considered to be transfection agents. In the embodiment of delivering RNA molecules by a recombinant viral vector, the gene delivery vector is a viral vector carrying a non-coding RNA molecule describe above in this invention. Gene delivery vectors include but not limited to vectors such as virus vector, collagens such as terminated peptide collagens, polymers such as polyethylenimine (PEI), polypeptides such as poly (L-lysine) and protamine, and liposomes such as Lipofectamine. Gene delivery vectors can be commercially available, such as transfection reagents from Thermo Fisher, U.S.A. including Lipofectamine RNAiMAX, Lipofectamine 3000, and Lipofectamine 2000; RNAi-Mate from GenePharma, China; terminated peptide collagens from Koken Co. Ltd, Japan; and histidine-lysine peptide copolymer from siRNAomics, China. Gene delivery vectors can be viral vectors based on retroviruses, adeno-associated viruses, adenoviruses, and lentiviruses. The gene delivery vector should be of a low toxicity and not induce significant immune response in subjects. In an embodiment, non-coding RNA molecule can be provided in a pharmaceutical composition comprising histidine-lysine polymer (HKP). HKP can encapsulate the non-coding RNA molecule to form nanoparticles that can deliver the RNA molecule to cells and enhancing the absorption of RNA molecule.

In an embodiment, the pharmaceutical composition may further comprise a nucleic acid stabilizer. The nucleic acid stabilizer refers to any chemicals that are capable of maintaining the stability of the RNA molecule in the composition to minimize or avoid degradation, in particular those having ability to deactivate activity of nucleases or the like degrading the RNA molecules.

Still further, this invention pertains to use of a nucleic acid molecule in the preparation of a medicament for preventing and/or treating cancer. The nucleic acid is a non-coding RNA molecule as described above including a functional variant or homologue thereof. It would also be appreciated that the non-coding RNA molecule of this invention can be used as a small interfering RNA molecule to interfere the expression of certain genes in the target cancer cells, thereby to cause gene silencing, apoptosis, inhibition of cell growth and proliferation, or the like to achieve the desired therapeutic effect.

Accordingly, this invention provides a novel and effective approach for treating cancers from various origins by administration the combination of a non-coding RNA molecule and an antibody targeting a tumor antigen. The administration of the combination of a non-coding RNA molecule and an antibody targeting a tumor antigen is also suitable for inhibiting growth, proliferation or metastasis of cancer cells or cancer tissues. The combination of a non-coding RNA molecule and an antibody targeting a tumor antigen are found to be highly effective at inhibiting growth and proliferation of in vitro and in vivo cancer cells or cancer tissues in mice. The RNA molecule can also effectively promote the proliferation of macrophages.

The invention is now described in the following non-limiting examples. The experimental methods in the following examples are conventional methods unless otherwise specified. The raw materials, reagent materials and the like used in the following examples are commercially available products unless otherwise specified.

EXAMPLES

Chemicals and Materials

Experimental animals: 110 healthy 8- to 10-week old female C57BL/6 mice (20-25 g) were purchased from the Animal Experimental Center of the Chinese University of Hong Kong, and maintained in the Animal Experimental Center of Macau University of Science and Technology.

Tumor cell line: LLC-LUC lung cancer cell line was purchased from the ATCC Biological Standards Resource Center of the United States and cultured in DMEM medium containing 10% fetal bovine serum.

Main reagents: RNA was synthesized by Suzhou Beixin Biotechnology Co., Ltd., HC58 sequence information: the sense strand (5'>3') CGCGGAGUAGAGCAGUUUG, derived from ginseng tRNAMet (CAU); the antisense strand (5'>3') CAAACUGCUCUACUCCGCG is its complementary sequence, forming transfer RNA fragments (tRF). Histidine-Lysine Polymer (HKP) was purchased from Suzhou Shengnuo Biomedical Technology Co., Ltd. Anti-mouse PD-1 antibody (anti-PD-1) was purchased from InvivoMab, USA (molecular weight is 150 kDa, product model is CD279, and the product information is available at https://bxcell.com/product/invivomab-anti-m-pd-1/).

Example 1

C57BL/6 Mouse Model of LLC-LUC Lung Cancer Xenograft

The LLC-LUC lung cancer cell lines were cultured in Dulbecco's Modified Eagle Medium (DMEM) containing 10% FBS and 1% penicillin/streptomycin at humidified atmosphere containing 5% $CO_2$ at 37° C. The cells in the logarithmic growth phase were centrifuged at 800 rpm/min for 5 min at 20° C., and the culture medium was removed. Then, sterilized saline (PBS) solution was added to wash the cells (centrifuged at 800 rpm/min at 20° C. for 5 min to remove the PBS solution), an appropriate amount of blank DMEM culture medium (without FBS and PS) was added, and the cells were dispersed to prepare a single cell suspension with a cell density of $1 \times 10^7$ cells/mL. One day before the inoculation of the tumor strain, the hair from the right forelimb axillary of the mouse was removed and 0.2 mL/mouse was inoculated under the skin of the right forelimb axillary of the mouse to construct a mouse subcutaneous xenograft animal model. The date was denoted as Day 1 (D1) when the tumor grew to ~60 $mm^3$.

Example 2

Preparation of HKP-tRF Nanoparticles

30 μg/mL HKP in RNase-free aqueous solution and 10 μg/mL tRF in RNase-free aqueous solution were mixed at a mass ratio of 3:1 in equal volumes, after vortexing for 5 seconds, the mixture was incubated at room temperature for 30 minutes to obtain HKP-tRF nanoparticle solution. The solution was diluted with normal saline to the required concentration and was vortexed well before administration. This HKP-tRF nanoparticles sample was abbreviated as RNA in subsequent examples.

Example 3

Grouping and Intervention

The tumor-bearing mice were randomly divided into seven groups: (A) anti-PD-1+RNA-L group, (B) anti-PD-1+RNA-H group, (C) anti-PD-1 group, (D) RNA-L group, (E) RNA-H group, (F) HKP group, and (G) model group.

(Group A and B): On D1, D4, D7, D10 and D13, anti-PD-1 was intraperitoneally injected at a concentration of 250 μg/0.2 mL for each mouse. On D1, D3, D5, D7, D9, D11 and D13, different concentrations of RNA (5 μg/mL for low-dose, and 10 μg/mL for high-dose) were administrated via intravenous tail injection at a dose of 50 μg/kg (low-dose) and 100 μg/kg (high-dose), respectively. (Group C): On D1, D4, D7, D10 and D13, anti-PD-1 was administered by intraperitoneal injection at a concentration of 250 μg/0.2 mL for each mouse. On D1, D3, D5, D7, D9, D11 and D13, normal saline at 0.01 mL/g was administrated via intravenous tail injection. (Group D and E): On D1, D4, D7, D10, and D13, 0.2 mL of normal saline was administered via intraperitoneal for each mouse. On D1, D3, D5, D7, D9, D11 and D13, different concentrations of RNA (5 μg/mL for low-dose, and 10 μg/mL for high-dose) were administered via intravenous tail injection at a dose of 50 μg/kg (low-dose) and 100 μg/kg (high-dose), respectively. (Group F): On D1, D4, D7, D10, and D13, 0.2 mL of normal saline was administered via intraperitoneal for each mouse. On D1, D3, D5, D7, D9, D11 and D13, HKP without RNA was administrated via intravenous tail injection at a dose of 300 μg/kg. (Group G): On D1, D4, D7, D10, and D13, 0.2 mL of normal saline was administered via intraperitoneal for each mouse. On D1, D3, D5, D7, D9, D11 and D13, normal saline at 0.01 mL/g was administrated via intravenous tail injection.

The weight of each mouse was recorded every day, while their tumor sizes were monitored with digital caliper every 3 days and expressed as volume (length×width×width/2). Mice were scarified before the end point if >20% weight loss occur, or the tumor reached the maximum permitted size (2000 $mm^3$) for each model. Survival data was obtained by observing the mice lifespan and Kaplan-Meier estimator was performed to plot a survival curve.

FIG. 1 shows the tumor growth curves of each group of models. The results showed that, the tumor volumes of the HKP group (group F) and the groups administrated with RNA alone (group D and E) have no significant differences when compared with that of the model group (group G). Besides, the tumor volumes of the anti-PD-1 group (group C) were significantly lower than that of the model group since D10 ($P<0.01$), and the P value was lower than 0.001 since D18. In addition, when compared with the model group, the tumor volumes of the combination group administrated with both anti-PD-1 and low-dose RNA (50 μg/kg) (group A) showed a significant reduction in tumor volume since D12 ($P<0.05$), and the P values were lower than 0.01 and 0.001 since D14 and D18, respectively; whereas the combination group administrated with both anti-PD-1 and high-dose RNA (100 μg/kg) (group B) also showed a significant reduction in tumor volume, the P values were lower than 0.01 and 0.001 since D6 and D10, respectively. Moreover, the tumor volume of the combination group administrated with both anti-PD-1 and high-dose RNA (100 μg/kg) were significantly lower than that of the anti-PD-1 group, the P value was lower than 0.05 at the fifth administration (D12), and the P values were lower than 0.01 afterwards (n=15).

Figure 3:
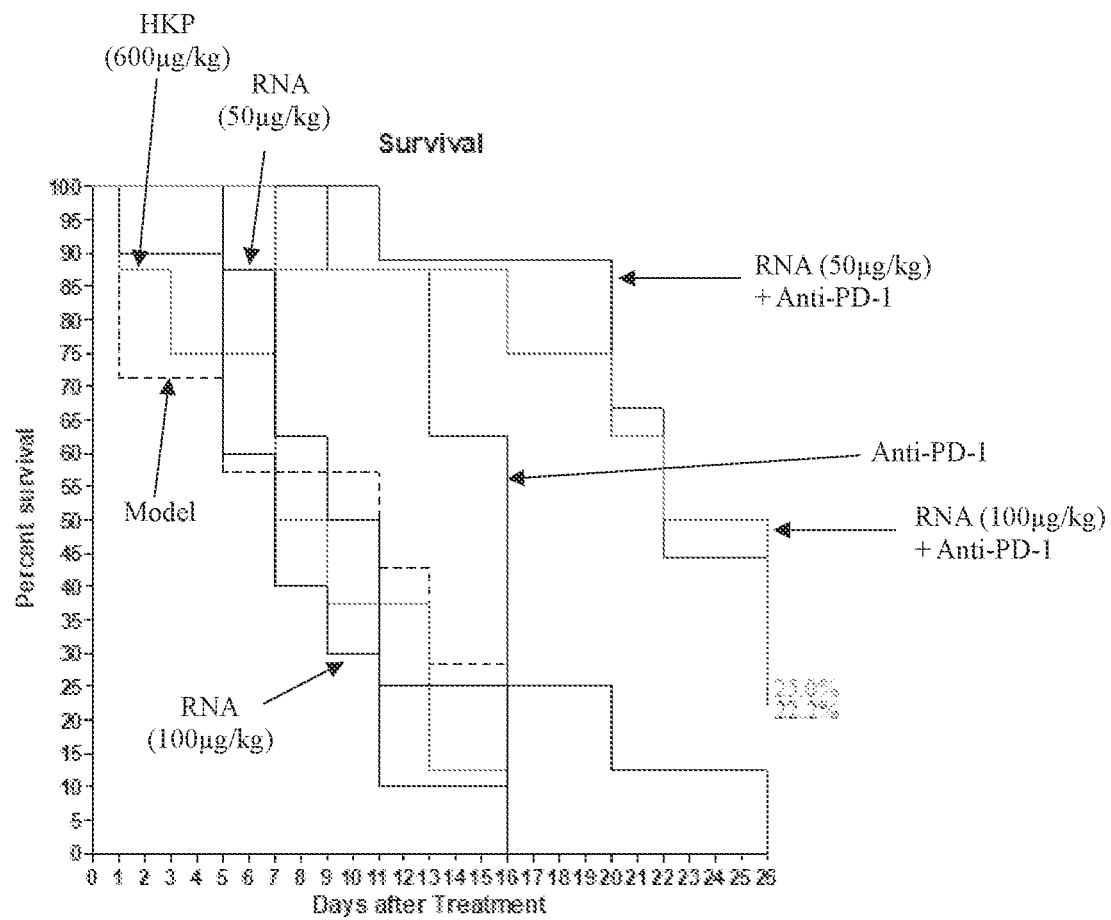
FIG. 3 shows the survival curves of each group of models.

The survival of mice in each group was observed every day after the construction of tumor-bearing model, and the survival rate was calculated. FIG. 3 shows the survival curve of each group of models. The results showed that the survival rate of mice in the HKP group and the groups administrated with RNA alone did not show significant differences when compared with that of the model group (black dotted line), the survival rate dropped to about 70% within D1 to D7, and it fell to below 30% within D7 to D13, and all mice died on D16. Meanwhile, the survival rate of mice in the anti-PD-1 group dropped to 70% on D13, and it fell to below 30% on D16, and all mice died on D26. In particular, the survival rate of the two combination groups administrated with both anti-PD-1 and RNA were not only higher than the control group and the RNA alone group, but also significantly higher than the anti-PD-1 group (P<0.05). The survival rate of both combination groups dropped to below 70% until D20, and the survival rates of those tumor-bearing mice were maintained at 22.2% and 25.0% at the end of the experiment (D26).

a 96-well microplate at a density of 5000 cells per well (100 μL) and allowed to adhere for 18 h before the treatment. The cells were given at different concentrations of HC58 RNA solution and cultured in a 37° C. incubator for 24 hours. After treating for 24 h, 100 μL MTT solution (0.5 mg/mL) was added to each well and incubated for 4 h at 37° C. Subsequently, 150 μL dimethyl sulfoxide (DMSO) was added and the optical densities of the resulting solutions were calorimetrically determined at 570 nm using a SpectraMax 190 microplate reader (Molecular Devices, Sunnyvale, CA, U.S.A). In addition, treatment with lipopolysaccharide (LPS) at 25 ng/mL was set as the positive control. Dose-response curves were obtained, and the IC50 values were calculated by GraphPad Prism 5 (GraphPad, La Jolla, CA, USA). Each experiment was carried out for three times. IC50 results were expressed as means±standard deviation.

Figure 2:
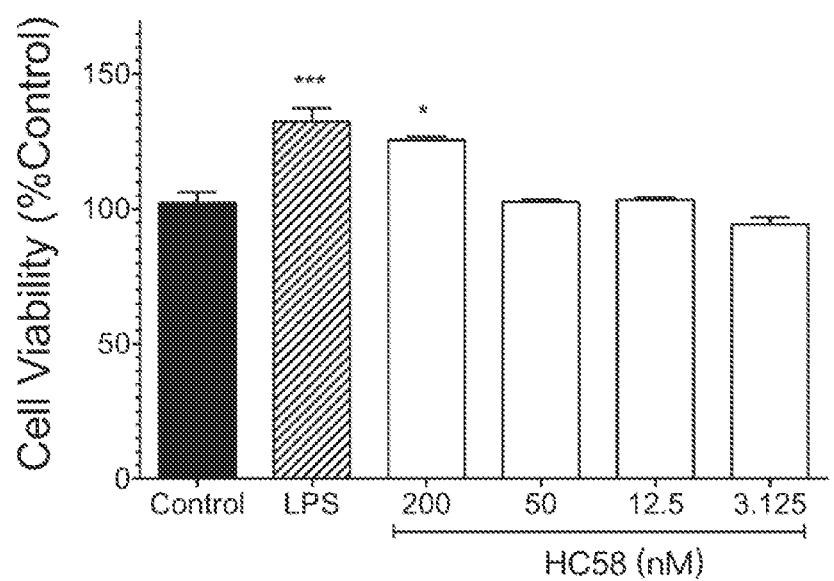
FIG. 2 shows the proliferation effect of HC58 on RAW264.7 macrophage cells.

FIG. 2 shows the proliferation effect of HC58 on RAW264.7 macrophage cells. The results showed that after treatment with four concentrations of HC58 at 200 nM, 50 nM, 12.5 nM, and 3.125 nM, HC58 at 200 nM exhibited a significant proliferation effect on RAW264.7 macrophage cells when compared with the control group (P<0.05). These results revealed that HC58 can enhance the anti-cancer activity of anti-PD-1 by promoting the proliferation of macrophages.

SEQUENCE LISTING

```
<160> NUMBER OF SEQ ID NOS: 2

<210> SEQ ID NO 1
<211> LENGTH: 19
<212> TYPE: RNA
<213> ORGANISM: Artificial Sequence
<220> FEATURE:
<223> OTHER INFORMATION: Synthesized

<400> SEQUENCE: 1
caaacugcuc uacuccgcg                                                   19

<210> SEQ ID NO 2
<211> LENGTH: 19
<212> TYPE: RNA
<213> ORGANISM: Artificial Sequence
<220> FEATURE:
<223> OTHER INFORMATION: Synthesized

<400> SEQUENCE: 2
cgcggaguag agcaguuug                                                   19
```

Example 4

The Effect of HC58 on the Proliferation of Macrophages

The RAW264.7 mouse macrophage cell lines were cultured in DMEM medium containing 10% FBS and 1% penicillin/streptomycin at humidified atmosphere containing 5% $CO_2$ at 37° C. In the cell viability assay, exponentially growing cells of RAW264.7 macrophage cells were plated in

The invention claimed is:

1. A medicinal composition for preventing and/or treating cancer comprising a non-coding RNA molecule and an antibody targeting a tumor antigen,
   wherein the non-coding RNA molecule is a tRNA molecule comprising an antisense strand having a sequence identity of at least 90% with respect to SEQ ID NO: 1, and a sense strand having a sequence identity of at least 90% with respect to SEQ ID NO: 2, and
   wherein the antibody targets a PD-1 tumor antigen; and
   wherein said non-coding RNA molecule and said antibody targeting a tumor antigen may be administered to a patient as a mixture of said non-coding RNA molecule and said antibody targeting a tumor antigen; or said non-coding RNA molecule and said antibody targeting a tumor antigen may be administered to a patient separately.

2. The medicinal composition of claim 1, wherein a mass ratio of the non-coding RNA molecule, and the antibody targeting a tumor antigen is between 1:250 and 1:100.

3. The medicinal composition of claim 1, further comprises a pharmaceutically acceptable carrier, a diluent or an excipient.

4. The medicinal composition of claim 3, wherein the pharmaceutically acceptable carrier is selected from the group consisting of a viral vector, a collagen, a polymer, a polypeptide, a protamine, a lipid-forming liposome, and any combination thereof.

5. The medicinal composition of claim 4, wherein the pharmaceutically acceptable carrier comprises a polypeptide or a histidine-lysine polymer.

6. The medicinal composition of claim 1, further comprises other medicine for preventing and/or treating cancer, and/or a nucleic acid stabilizer.

7. The medicinal composition of claim 1, wherein the medicinal composition has a dosage form for subcutaneous, intravenous, intraperitoneal or intramuscular injection.

8. A kit comprising a medicinal composition according to claim 1.

9. The kit of claim 8, wherein the non-coding RNA molecule and the antibody targeting a tumor antigen are provided in separate containers, and each of them is provided in a dosage form for subcutaneous, intravenous, intraperitoneal or intramuscular injection.

10. The medicinal composition of claim 2, wherein the mass ratio of the non-coding RNA molecule, and the antibody targeting a tumor antigen is 1:125.

11. The medicinal composition of claim 1, wherein the non-coding RNA molecule is a double-stranded tRNA molecule.

12. The medicinal composition according to claim 3, wherein the pharmaceutically acceptable carrier comprises a gene delivery vector or a material encapsulating the non-coding RNA molecule to form nanoparticles.

13. The medicinal composition of claim 1 wherein the non-coding RNA molecule is a tRNA molecule consisting of an antisense strand having a sequence identity of at least 90% with respect to SEQ ID NO: 1, and a sense strand having a sequence identity of at least 90% with respect to SEQ ID NO: 2.

14. The medicinal composition of claim 1 wherein said antisense strand is SEQ ID NO: 1.

15. The medicinal composition of claim 1 wherein said sense strand is SEQ ID NO: 2.

* * * * *